US00PP35955P2

(12) United States Plant Patent
Xiangang et al.

(10) Patent No.: US PP35,955 P2
(45) Date of Patent: Jul. 2, 2024

(54) ***HOYA* PLANT NAMED 'JAD037'**

(50) Latin Name: *Hoya ilagiorum*
Varietal Denomination: JAD037

(71) Applicant: Anhui Jadeite Garden Co., Ltd, Chuzhou (CN)

(72) Inventors: Shen Xiangang, Chuzhou (CN); Zhang Xueping, Chuzhou (CN); Qian Jingjing, Chuzhou (CN)

(73) Assignee: Anhui Jadeite Garden Co., Ltd. (CN)

( * ) Notice: Subject to any disclaimer, the term of this patent is extended or adjusted under 35 U.S.C. 154(b) by 0 days.

(21) Appl. No.: 18/372,216

(22) Filed: Sep. 25, 2023

(51) Int. Cl.
*A01H 5/02* (2018.01)
*A01H 6/08* (2018.01)

(52) U.S. Cl.
USPC ..... Plt./380
CPC ..... *A01H 6/08* (2018.05)

(58) Field of Classification Search
USPC ..... Plt./380
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Hoya* plant named 'JAD037' is disclosed, characterized by table marginal cream colored foliage variegation and flower buds which are uniquely striped creamy white. The new variety is a *Hoya*, typically produced as an indoor ornamental plant.

2 Drawing Sheets

Latin name of the genus and species: *Hoya ilagiorum.*
Variety denomination: 'JAD037'.

BACKGROUND OF THE INVENTION

The new cultivar is a spontaneous whole plant mutation. The new variety was discovered by the inventors in an existing population of unpatented, unnamed *Hoya ilagiorum* plants in May 2020 at a nursery in Chuzhou, China.

Asexual reproduction of the new cultivar 'JAD037' was first performed in Chuzhou, China by terminal vegetative cuttings in 2021. Subsequent asexual propagation has shown that the unique features of this cultivar are stable and reproduced true to type.

The following traits have been repeatedly observed and are determined to be the unique characteristics of 'JAD037'. These characteristics in combination distinguish 'JAD037' as a new and distinct *Hoya* cultivar:

1. Stable marginal cream colored foliage variegation.
2. Flower buds with distinct creamy white stripes.

PARENT COMPARISON

Plants of the new cultivar 'JAD037' are similar to the parent in most horticultural characteristics. The new variety, however, differs in the following:

1. The new variety has cream colored foliage variegation; the parent variety has solid green foliage.

COMMERCIAL COMPARISON

'JAD037' can be compared to compared to the commercial variety *Hoya* 'Amore Variegata', unpatented. Plants of 'Amore Variegated' are similar to plants of 'JAD037' in most horticultural characteristics, including having creamy marginal foliage variegation, however, plants of 'JAD037' differ in the following:

1. Foliage of 'JAD037' is narrower and glossier than foliage of 'Amore Variegata'.
2. Foliage color of 'JAD037' is Green 141A with marginal coloration Yellow 4D; foliage color of 'Amore Variegata' is Green N138B with marginal coloration Yellow 4D.

BRIEF DESCRIPTION OF THE PHOTOGRAPHS

Figure 1:
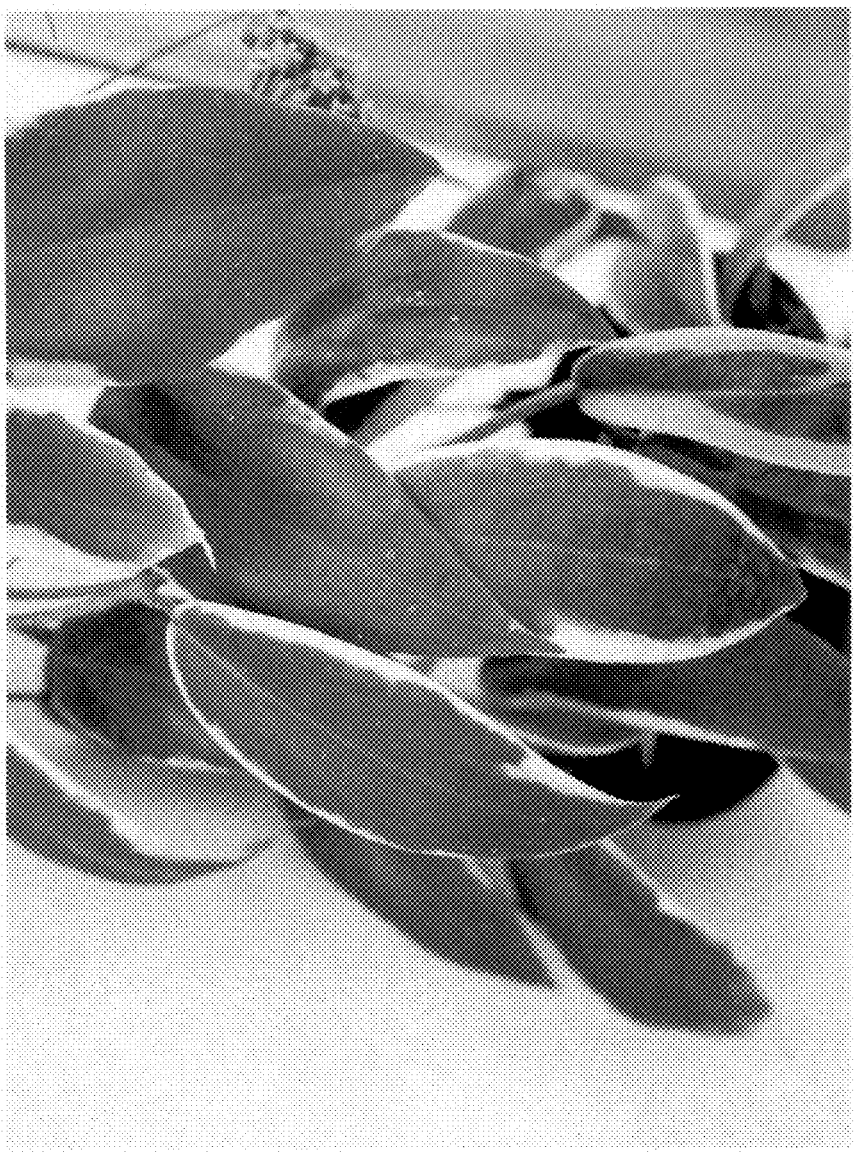

The accompanying drawing in FIG. 1 illustrates in full color the typical characteristic foliage of 'JAD037'.

Figure 2:
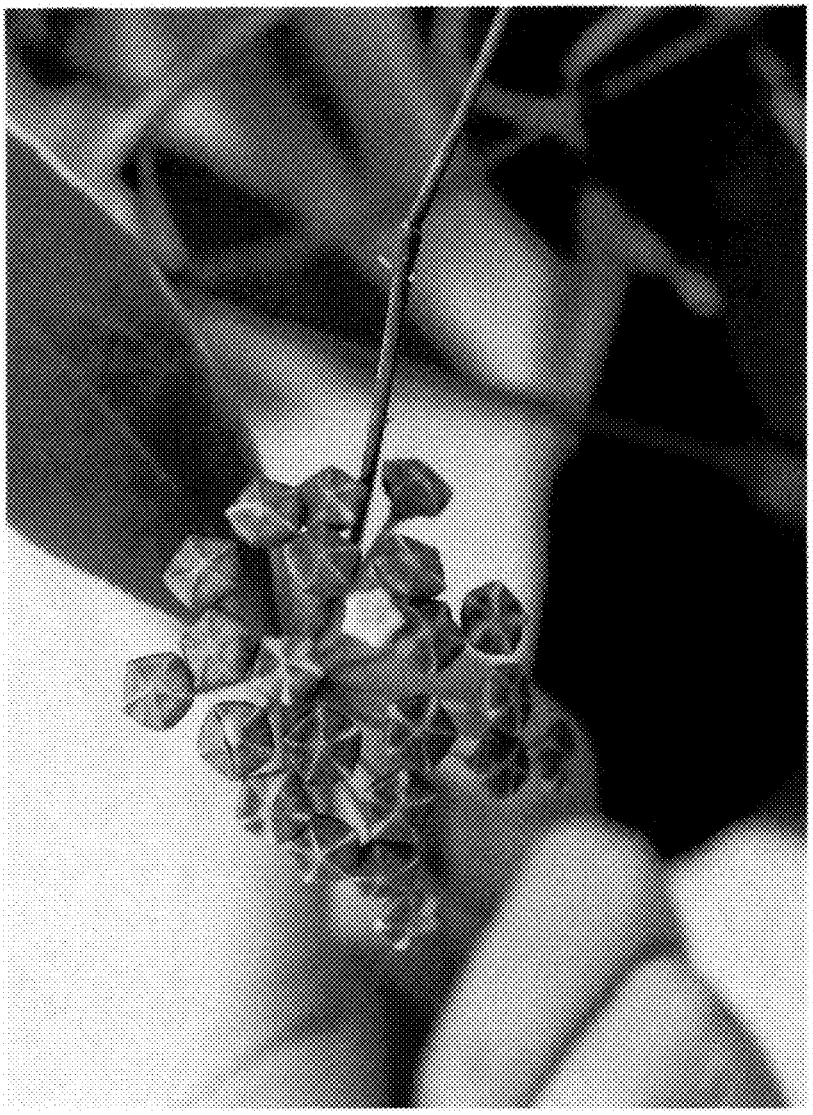

FIG. 2 is a close-up view of the flower buds. Plants were grown in a greenhouse in Chuzhou, China and approximately 2 years old when photographed. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'JAD037' plants grown in a greenhouse in Chuzhou, China. Temperatures ranged from 22° C. at night to 26° C. during the day. No artificial light, photoperiodic treatments were given to the plants. Measurements and numerical values represent averages of typical plant types. Botanical classification: *Hoya ilagiorum* 'JAD037'.

PROPAGATION

Time to initiate roots: About 15 days at approximately 30° C. in the summer. About 25 days at 18° C. in the winter.

Time to produce a rooted cutting: About 50 days at 20° C. to 30° C.

ROOTS

Root structure:
*Average length.*—20 cm.
*Average diameter.*—0.1 cm.
*Type.*—Fleshy.
*Color.*—RHS White 155B.

PLANT

Plant type: Tender perennial flowering vine.
Age of plant described: 2 years.
Container size: 10 to 15 cm.
Height: 40 cm to top of foliar plane; 28.5 cm to top of floral plane.
Plant spread: 32.5 cm.
Growth rate: High.
Plant vigor: High.
Branching characteristics: Basal; no pinching required.
Length of primary lateral branches: About 40 cm.
Diameter of lateral branches: About 5 to 9 mm.
Internode length: 6.5 cm.
Stem:
*Aspect.*—Spread.
*Strength.*—Weak.
*Pubescence.*—None.
*Luster.*—Semi-glossy.
*Color.*—Developing: RHS Brown N199B. At Internodes: RHS Brown N199A. Developed: RHS Yellow-Green 148B.

FOLIAGE

Leaf:
*Arrangement.*—Opposite, single.
*Length.*—12.9 cm.
*Width.*—4.8 cm.
*Shape of blade.*—Lanceolate.
*Apex.*—Acute.
*Base.*—Obtuse.
*Margin.*—Entire.
*Texture.*—Fleshy, both surfaces.
*Pubescence.*—None.
*Rugosity.*—Smooth.
*Luster.*—Upper Side: High. Under Side: Weak.
*Color.*—Young Foliage, Upper Side: Narrow Edge: RHS Purple-Red 70B. Center: RHS Yellow-Green 147A. Young Foliage, Under Side: Narrow Edge: RHS Purple 75A. Center: RHS Yellow-Green 146B. Mature Foliage, Upper Side: Narrow Edge: RHS Yellow 4D. Center: RHS Green 141A. Mature Foliage, Under Side: Narrow Edge: RHS Yellow 4D. Center: RHS Green 138B. Autumn Foliage, Upper Side: Narrow Edge: RHS Yellow 4D. Center: RHS Yellow-Green 141A. Autumn Foliage, Under Side: Narrow Edge: RHS Yellow 4D. Center: RHS Green 138B.
*Venation.*—Type: Pinnate. Color Upper Side: RHS Yellow-Green 141A. Color Under Side: RHS Yellow-Green 140A.
*Petiole.*—Length: 1.6 to 2 cm. Diameter: 0.3 to 0.6 cm. Color, Upper Side: RHS Brown 199D. Color, Under Side: RHS Brown 199B. Texture: Fleshy. Luster: Weak. Strength: Medium.

FLOWER

Natural flowering season: All year.
Flower arrangement: Cymose umbel.
Flower type and form: Hemisphere.
Inflorescence type and form: Umbelliform.
Quantity of inflorescences per plant: 3 to 6.
Quantity of flowers: 18 to 23 per inflorescence.
Quantity of buds: 18 to 23 per flower.
Flower longevity: 4 to 7 days.
Inflorescence size:
*Diameter.*—0.5 to 0.6 cm.
*Height.*—9.1 cm.
Bud:
*Shape.*—Pentagon.
*Length.*—0.3 to 0.5 cm.
*Diameter.*—0.5 to 0.7 cm.
*Color.*—RHS Red-Purple 60A striped White 155C.
*Texture.*—Fleshy.
*Luster.*—Weak.
Flower:
*Shape.*—Star.
*Height.*—2.6 cm.
*Diameter.*—0.8 cm.
*Length.*—0.6 cm.
Petals:
*Arrangement.*—Double whorl.
*Quantity.*—10 per flower.
*Shape.*—Ellipse.
*Length.*—Corolla 0.4 cm; corona 0.3 cm.
*Width.*—Corolla 0.4 cm; corona 0.2 cm.
*Margin.*—Entire, undulate.
*Apex.*—Acute.
*Base.*—Fused.
*Texture, both sides.*—Corolla: fleshy; corona: leathery.
*Rugosity, both sides.*—Corolla: smooth; Corona: smooth.
*Luster, both sides.*—Corolla: high; Corona: high.
*Color.*—When opening: Upper surface: Corolla: RHS Red-Purple 60A; Corona: Purple 69A. Lower surface: Corolla: RHS Greyed-Red 182A; Corona: Purple 69A. Fully opened. Upper surface: Corolla: RHS Red 60A; Corona: Purple 69A. Venation: Corolla: RHS Red 60A; Corona: Purple 69A. Lower surface: Corolla: RHS Red 182A; Corona: Purple 69A. Venation: Corolla: RHS Red 182A; Corona: Purple 69A. Fading: Upper surface: Corolla: RHS Orange N170A; Corona: White 155D. Lower surface: Corolla: RHS Orange N170A; Corona: White 155D.
Sepals:
*Arrangement.*—Single whorl.
*Shape.*—Narrow ovate.
*Quantity.*—5 per flower.
*Length.*—0.2 cm.
*Width.*—0.1 cm.
*Margin.*—Entire.
*Apex.*—Acute.
*Base.*—Fused.
*Texture, both sides.*—Papery.

*Luster, upper side.*—Medium.
*Luster, under side.*—Weak.
*Color.*—When opening: Upper Surface: RHS Purple 77C. Lower Surface: RHS Purple N80D. Fully opened: Upper Surface: RHS Purple N80D. Lower Surface: RHS Purple N80D.

Calyx:
*Shape.*—Narrow ovate.
*Length.*—0.2 cm.
*Diameter.*—0.3 cm.

Peduncles:
*Length.*—2 to 6 cm.
*Width.*—0.2 cm.
*Angle.*—45° to 90°.
*Strength.*—Weak.
*Texture.*—Fleshy.
*Luster.*—Weak.
*Color.*—RHS Brown N200A.

Pedicels:
*Length.*—1.6 to 2 cm.
*Diameter.*—0.1 cm.
*Aspect.*—135° to 165°.
*Strength.*—Weak.
*Texture.*—Fleshy.
*Luster.*—Weak.
*Color.*—RHS Purple N79B.

Fragrance: Moderate, floral.

REPRODUCTIVE ORGANS

Androecium:
Stamens: Appressed to stigma, no distinguishable parts.
*Pollen amount.*—Low.
*Pollen color.*—Yellow, near 7B.

Gynoecium:
Pistil:
*Number.*—1.
*Length.*—0.1 cm.
*Stigma.*—Shape: Oval. Diameter: 0.1 cm. Color: White, too minute to identify with a color chart. Ovary Color: RHS Yellow 162D.

OTHER CHARACTERISTICS

Disease resistance: High resistance to normal diseases and pests of *Hoya* have been observed.

Drought tolerance and cold tolerance: Tolerates temperatures from approximately 3° C. to 45° C. Moderate tolerance to rain. High tolerance to wind.

Fruit/seed production: Not observed.

What is claimed is:

1. A new and distinct cultivar of *Hoya* plant named 'JAD037' as herein illustrated and described.

* * * * *